United States Patent [19]

Bedner et al.

[11] Patent Number: 4,846,250

[45] Date of Patent: Jul. 11, 1989

[54] METHOD OF CASTING A HANDLE FOR A SURGICAL BLADE

[76] Inventors: Richard J. Bedner, 113 Smoke Rise Dr., Warren, N.J. 07060; Emil Yerman, 2348 Terrace Ave., South Plainfield, N.J. 07080

[21] Appl. No.: 258,645

[22] Filed: Oct. 17, 1988

Related U.S. Application Data

[63] Continuation-in-part of Ser. No. 14,589, Feb. 13, 1987, Pat. No. 4,798,000.

[51] Int. Cl.⁴ .............................................. B22D 25/00
[52] U.S. Cl. ...................................... 164/47; 164/137; 164/271
[58] Field of Search .......................... 164/47, 137, 271

[56] References Cited

U.S. PATENT DOCUMENTS 3,311,976  4/1967  Matwijcow ........................... 30/335

FOREIGN PATENT DOCUMENTS 90337    1/1961  Denmark ............................. 164/271
57-8040  1/1982  Japan ..................................... 164/47

Primary Examiner—Nicholas P. Godici
Assistant Examiner—J. Reed Batten, Jr.
Attorney, Agent, or Firm—Robert A. Green

[57] ABSTRACT

The handle is made by casting in a two part mold. The lower mold part includes a vertical split post having two vertical spaced posts with their upper ends in the form of lateral tabs. The upper mold part has a flat wall member cooperating with the lateral tabs.

2 Claims, 5 Drawing Sheets

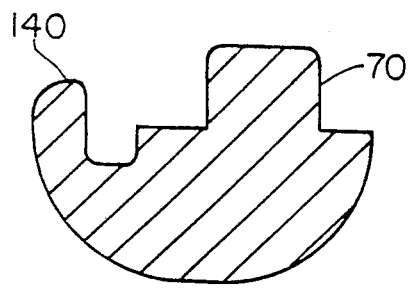
Fig. 4
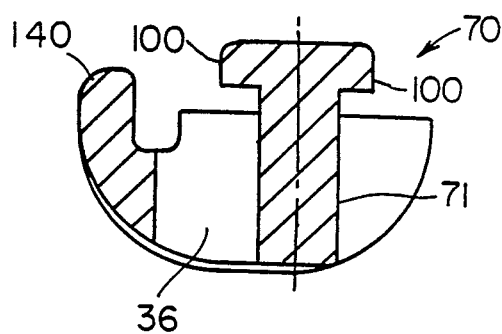
Fig. 5
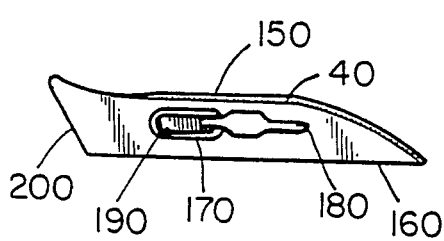
Fig. 6
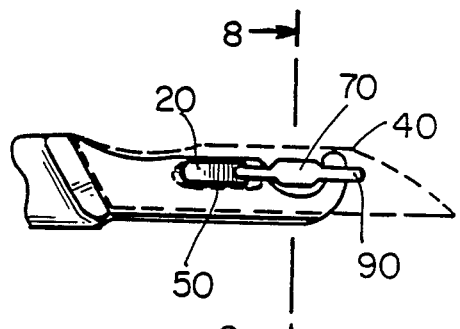
Fig. 7
Fig. 8
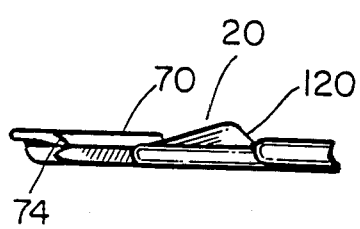
Fig. 9

METHOD OF CASTING A HANDLE FOR A SURGICAL BLADE

CROSS REFERENCE TO RELATED APPLICATIONS

This application is a continuation-in-part of application Ser. No. 07/014,589 filed Feb. 13, 1987 and now U.S. Pat. No. 4,798,000 issued January 17, 1989.

BACKGROUND OF THE INVENTION

At the present time, surgical scalpels comprise a handle to which cutting blades are attached. The handles may be of plastic but the preferred handle is made of metal because the weight and rigidity of metal assist the surgeon in operating. Because of this, the typical handle requires some machining to form parts to which a blade can be secured and as a result, the handle is relatively expensive and is not considered a disposable device.

SUMMARY OF THE INVENTION

The present invention provides a handle for a detachable surgical blade, the handle being of metal but being so constructed that it lends itself to lower-cost manufacturing methods than prior art metal handles. Although the handle is inexpensive enough to be disposable, it is so constructed that it can be re-used for a relatively large number of times. In addition, the handle of the invention provides improved support for surgical blades of different sizes.

DESCRIPTION OF THE DRAWINGS

FIG. 4 is a sectional view along the lines 4—4 in FIG. 1;

FIG. 5 is a sectional view along the lines 5—5 in FIG. 1;

FIG. 6 is a plan view of a cutting blade usable with the handle of the invention;

FIG. 7 is a plan view of the front end of the handle of FIG. 1 showing a blade coupled thereto;

FIG. 8 is a sectional view along the lines 8—8 in FIG. 7;

FIG. 9 is a side elevational view of a portion of the handle of FIG. 1;

DESCRIPTION OF THE INVENTION

The principles of the invention are described illustrated with respect to a surgical scalpel and the handle thereof but it will be clear to those studying the invention that these principles may be employed in other areas.

Figure 1:
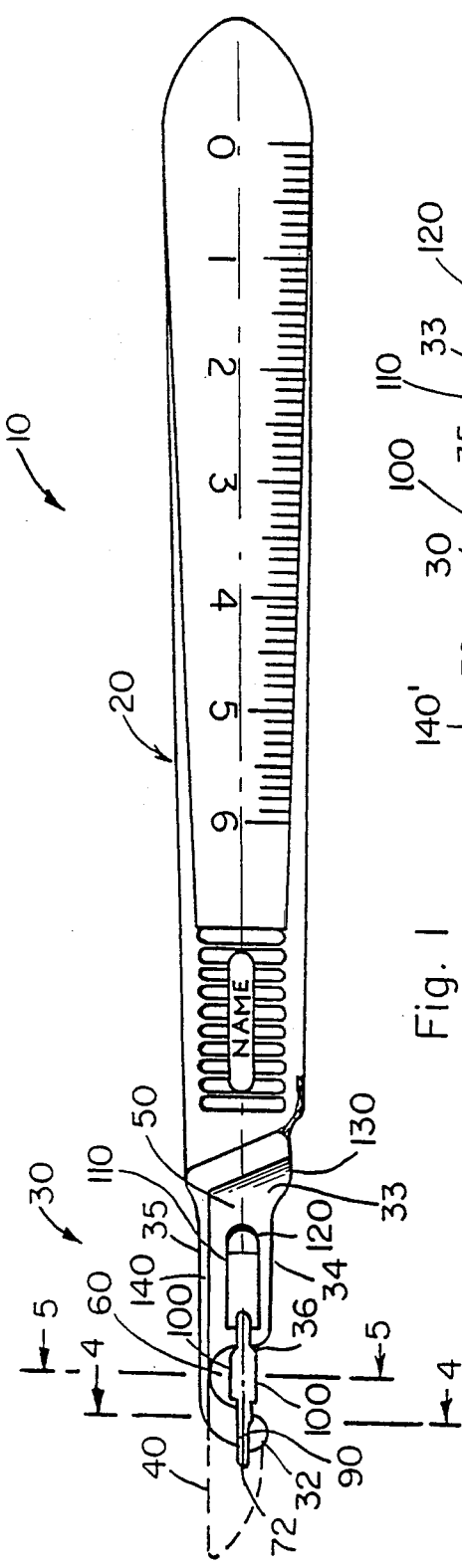
FIG. 1 is a plan view of a scalpel handle embodying the invention.
Figure 2:
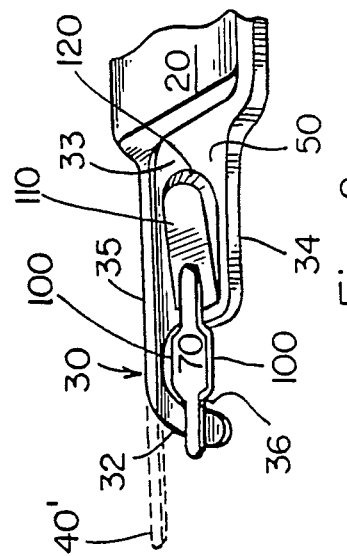
FIG. 2 is a perspective view of the blade support, front end, of the scalpel handle of FIG. 1.
Figure 3:
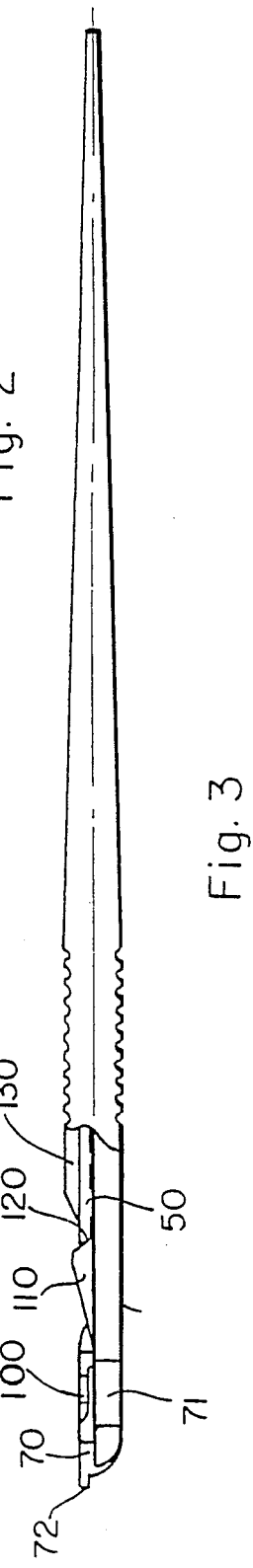
FIG. 3 is a side elevational view of the handle of FIG. 1.

A detachable cutting blade assembly 10, referring to FIG. 1, includes a handle having a front end 30 to which a cutting blade 40 can be detachably secured. The front end 30 of the handle has a smaller thickness than the rest of the handle and it includes a leading tip end 32, a rear end 33, a lower edge 34 and an upper edge 35. A generally U-shaped opening or hole 36 is provided in the front end of the handle, toward the leading tip end thereof and extending inwardly from the lower edge 34 to near the upper edge 35. The front end 30 of the handle has a generally flat top surface 50 and bottom surface 51 and a blade-locking member 70 extends along the top surface 50, lying along the long axis of the handle. The blade-locking member comprises a generally vertical wall (FIGS. 3 and 4) which rises from the top surface 50 and extends along a portion of the top surface 50 from the leading tip end 32 to near the center thereof. The blade-locking member 70 includes lips 100 (FIGS. 1, 2 and 5) which extend laterally from the upper and lower edges (as seen in FIG. 1) of the top surface of the locking member wall to give the locking member a T-shaped cross section (FIG. 5) which can engage and couple to and hold a surgical blade, with lips 100 holding the blade. The lips 100 lie within the area of the hole 36 as can be seen in FIG. 5 which is a view looking upwardly from the bottom of the front end (FIG. 4) of the handle through the hole 36 which extends through the body of the front end of the handle from the top surface 50 to the bottom surface 51. In addition, the locking member includes a wall portion 71 which extends down into and across the hole 36 as seen in FIGS. 3 and 5. The utility of this arrangement is discussed below and relates to the manufacture of an inexpensive handle.

The tip 72 of the locking member 70 may extend slightly beyond the leading tip end of the front end 30 itself.

Rearwardly of the locking member 70, the top surface 50 of the front end 30 carries a ramp 110 which rises from the top surface as it proceeds rearwardly aligned with the locking member and the long axis of the handle. At its rear end, the ramp 110 terminates in a wall which is also in the form of a ramp 120 which slopes downwardly toward the rear end 33 of the front end of the handle. The rear end of the front end of the handle terminates at a slanted surface or wall 130 (slanted at an angle to the longitudinal axis of the handle) against which a surgical blade 40 rests when it is coupled to the handle.

The front end of the handle also includes a wall 140 which extends along the upper edge 35 and rises above the top surface 50. The wall 140 provides a shoulder against which a surgical blade bears when secured to the handle.

The front end of the handle and the above described locking member 70 and ramp 110 carried thereby are shaped to provide locking engagement with standard surgical blades 40 which, at the present time, are all generally of the same construction. All such blades (FIG. 6) have a slot which permits them to be coupled to a handle. A typical surgical blade 40 includes a lower cutting edge 150 and an opposite upper edge 160 and a longitudinal slot 170 used in coupling the blade to the handle 20. The slot 170 includes a narrow front portion 180 which receives the locking member 70 and slips under the lips 100 and is held in place thereby. The rear portion 190 of the slot 170 is wider to receive the ramp 110 and is about the same width as the the ramp 110.

Referring to FIGS. 7 and 8 in coupling the blade 40 to the handle 20, the blade is seated on the front end 30 with the locking member 70 in the wide rear portion 190 of the slot 170 and it is pushed rearwardly. The rear portion of the blade slides up the ramp 110 thereby facilitating the operation and the narrow portion 180 of the slot 170 slips under lips 100 and engages the locking member 70. When the blade is in place, the rear edge of the slot 170 slides down the end ramp 120 to a final position determined by the total length of the slot 170.

It can be seen that the end ramp 120 provides tolerance for variations in the length of the slot 170 from blade to blade. If the slot is slightly short, the rear end of the slot stops in contact with an upper portion of the rear or end ramp and if the slot is somewhat larger, the rear end of the slot moves farther down the end ramp but always in contact therewith.

The rear end or edge 200 of the blade 40 is slanted to bear against and match the slant of the slanted wall 130 of the handle and the upper edge 160 of the blade bears against the upper wall or vertical tip 140 of the front end of the handle. The tip 72 and leading end 90 of the locking member 70 provide a stiffening support against which the blade 40 bears in use.

In a modification of the invention illustrated by dash lines in FIG. 1, the upper wall 140 of the front end of the handle is extended forwardly a suitable distance to provide an extended wall 140′. The wall 140′ provides support for especially large or long surgical blades. Wall 140′ may extend an additional ½″ or 1″ or more or less as required.

Under some circumstances, if the handle 20 is used as a disposable, the top of ramp 120 may be deformed by pressure to overlay the portions of the slot 190 in the blade 40 and thus provide additional locking means for holding the blade in place.

Normally, if it were desired to cast a handle 20 having a front end 30 of the type described above, including the locking member 70 having lips 100 and a T-shaped cross section, a multi-part mold would be required, including a removable rod to form the T-shaped portion of the locking member. This is a relatively complex and expensive casting operation. However, the provision of the hole 36 aligned with the lips 100 permits a relatively inexpensive two-part mold to be used. One part of the mold includes two posts which form the hole 36 and cooperate with the second part of the mold to form the lips 100 on the locking member.

Figure 10:
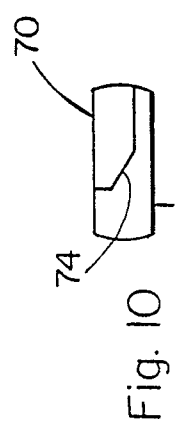
FIG. 10 is an enlarged view of a portion of the handle of the invention showing a modification of a portion thereof.

In a modification of the invention, the front end of the "T" structure of the blade locking member 70 formed by the lips 100 is tapered and provided with a sloped front wall 74 having a negative slope as seen in FIG. 10. The wall 74 thus slopes downwardly and rearwardly and this slope allows a blade to align itself as it is coupled to the handle 20.

Figure 11:
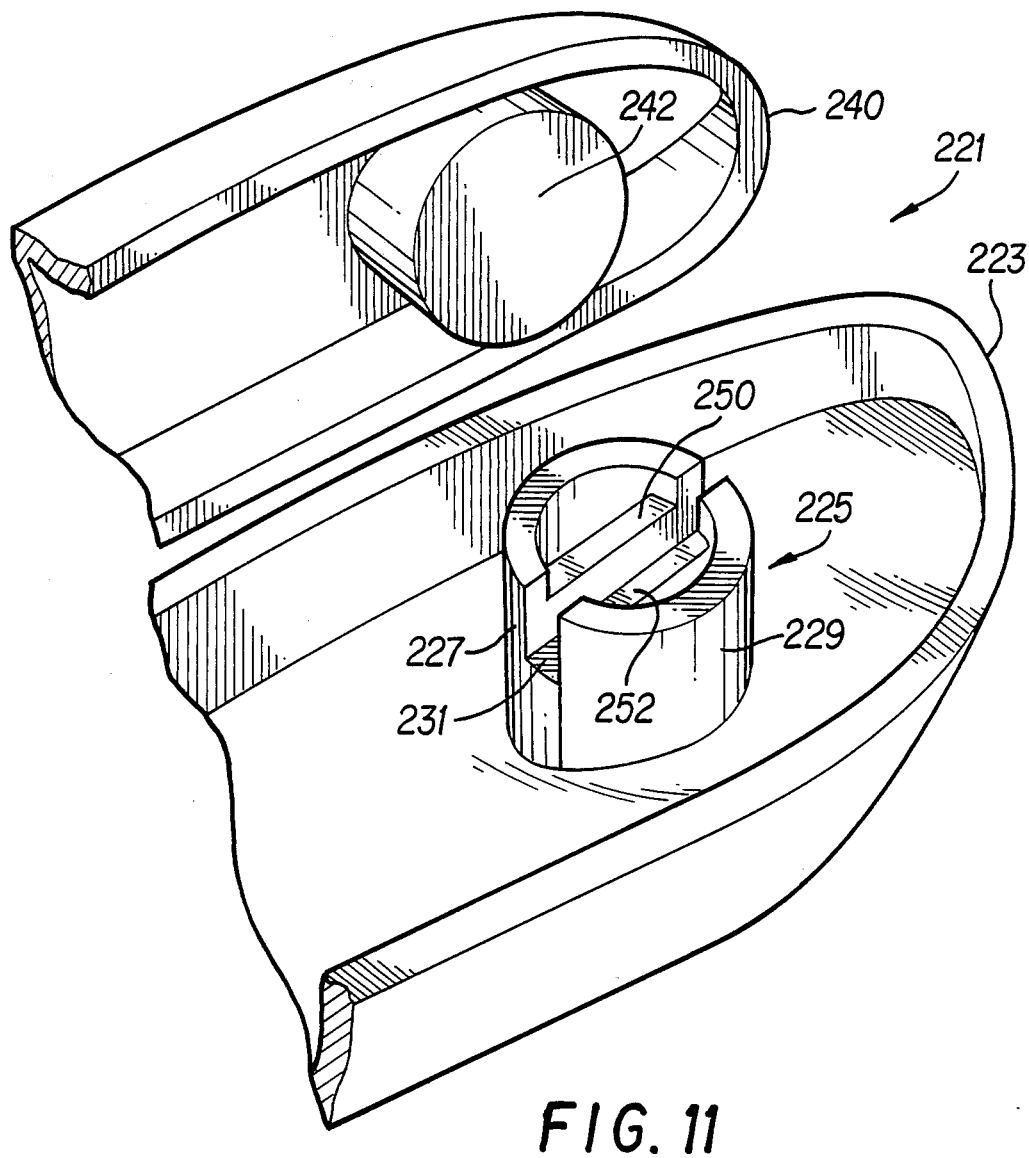
FIG. 11 is an exploded view of a two-part mold used in the method of the invention.

The surgical handle 20 can be made by completely conventional and well-known casting apparatus except for the inclusion in such apparatus of means for forming the hole 60, the locking member 70 and the lips 100 thereof. Thus, referring to FIGS. 11, 12 and 13, the handle 20 is made, according to the invention, by means of a simple two-part mold 221 which includes a lower mold portion 223 having the necessary structural features to form the lower portion of the handle 20. This lower mold portion includes at its front end, where the front end 30 of the handle is formed, a vertically oriented split pin 225. The split pin includes two vertical posts 227 and 229 having a space 231 between them. The top surfaces 233 and 235 of the posts 227 and 229 are coplanar and cutouts are formed therein adjacent to space 231 and extending downwardly to provide two horizontal coplanar surfaces or ledges 250, 252 disposed a suitable distance below the top surfaces 233 and 235. The cutouts form the tabs 100 in the final locking member 70 during the casting process.

The upper part 240 of the mold 221 includes a post or plug 242 having a flat lower surface 243 which is adapted to seat on the top surfaces 233 and 235 of the pins 227 and 229 to form the flat top surface of the tabs 100 with the tabs themselves being formed in the space beneath the post 242 and the surfaces 250 and 252. Under some circumstances, it may be desirable to make the post 242 adjustable by means of a threaded post secured to it whereby its position with respect to the split pin 225 can be adjusted.

Figure 12:
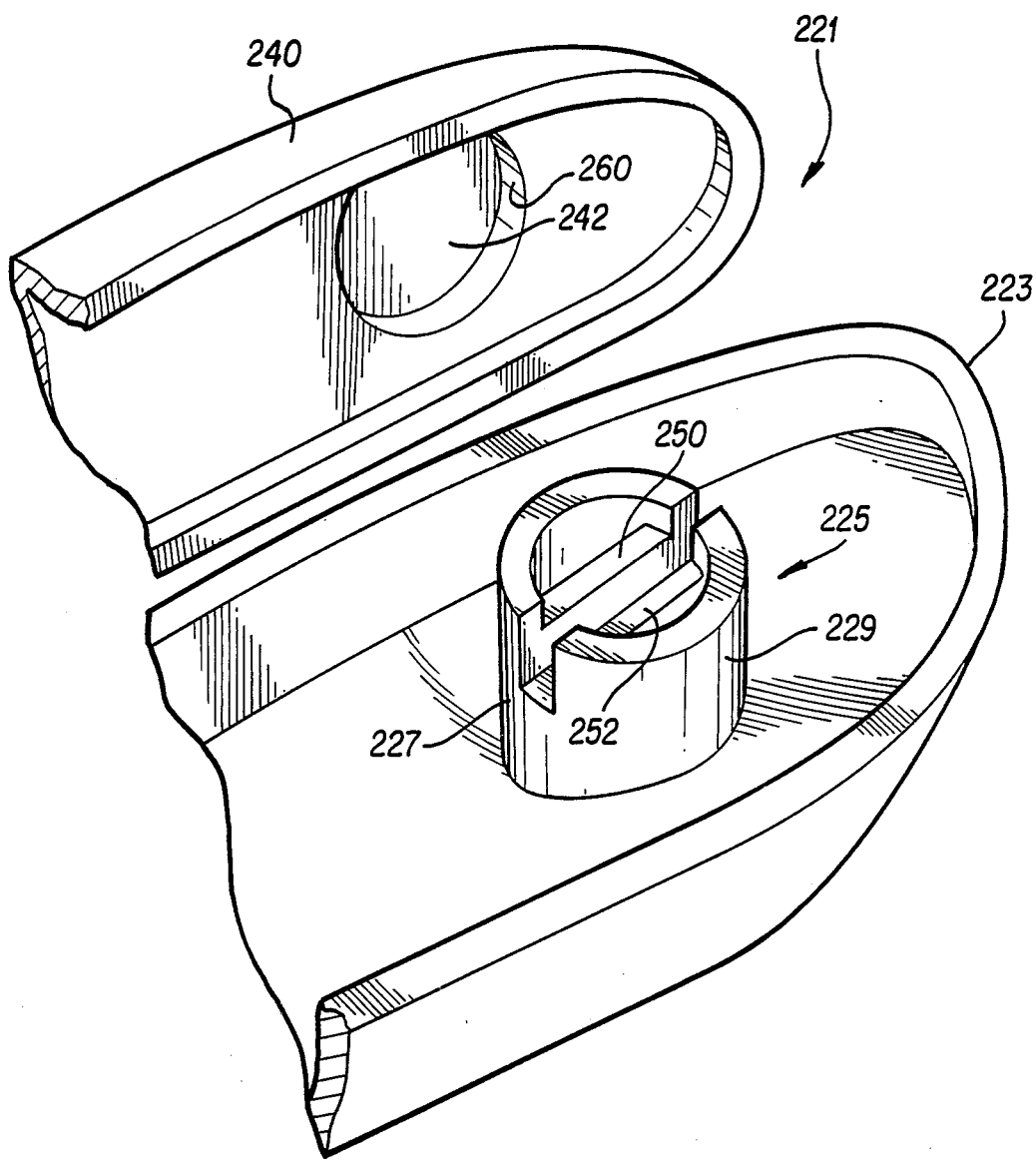
FIG. 12 is an exploded view of the mold of FIG. 11 showing a modification thereof.
Figure 13:
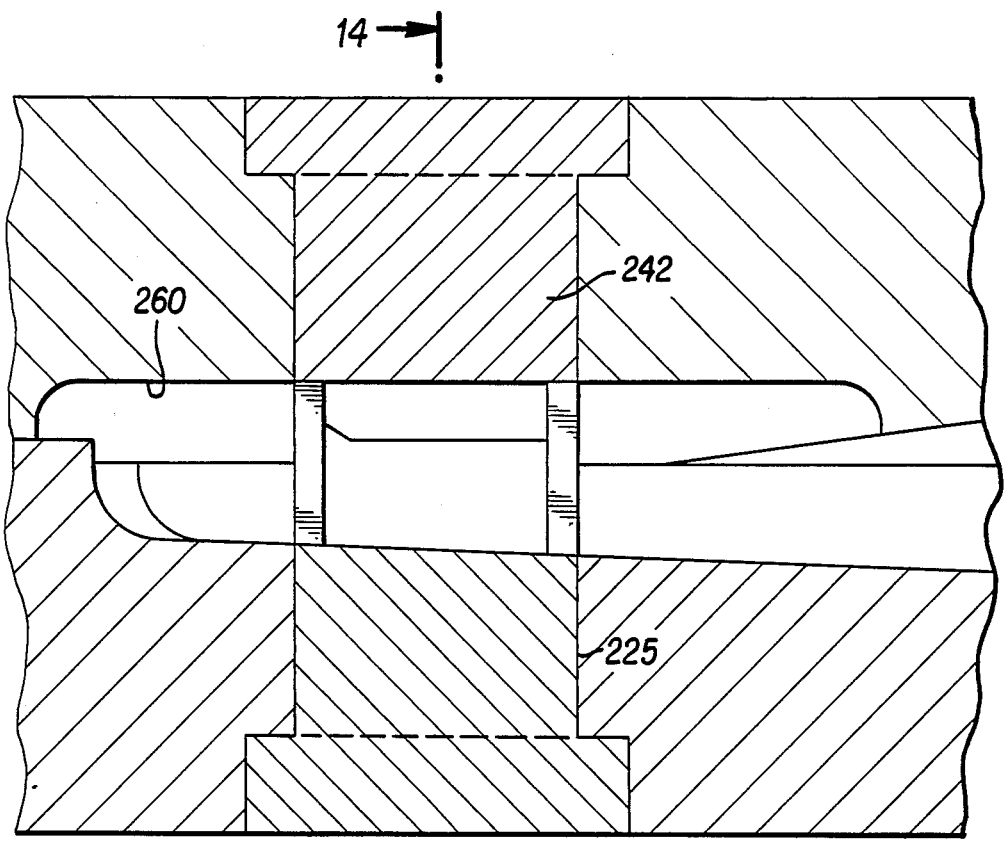
FIG. 13 is a side sectional elevational view of a portion of the mold of FIG. 12 showing the two parts of the mold assembled in operative relation.
Figure 14:
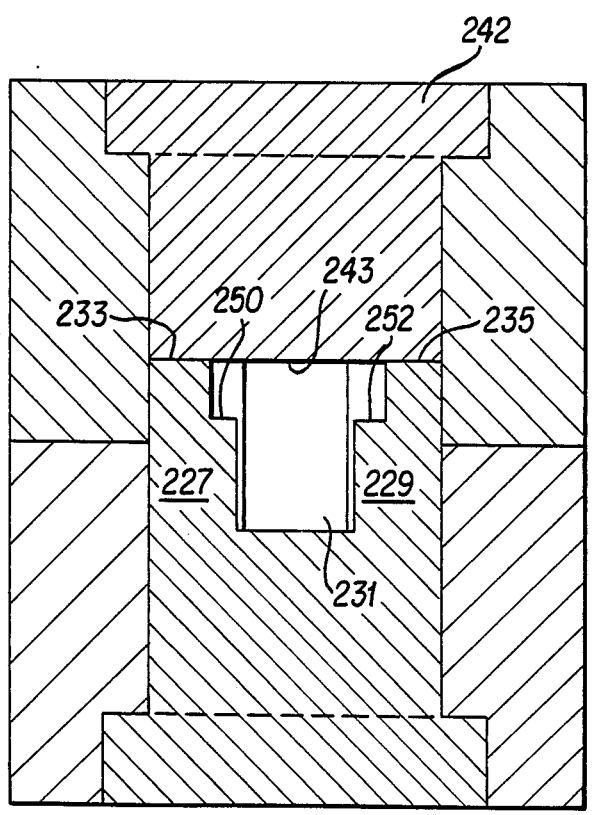
FIG. 14 is a sectional view along the lines 14—14 in FIG. 13.

In another configuration of the upper portion of the mold, shown in FIGS. 12 and 13, the upper flat ended post 242 is recessed in a cavity 260 into which the split pin 225 is inserted to bear against post 242 when the two parts of the mold are assembled to carry out the casting operation.

When metal is poured into the mold 221 to make a handle 20, the various parts of the handle are formed and the split pin 225 forms the hole 60, the vertical wall of the blade locking member 70 and the locking tabs 100.

The mold is used in conventional fashion and when molten metal is poured into the mold, all parts of the handle are formed which are described above and shown in the drawings. It is noted that this method of manufacture of a handle for a surgical blade may be used to manufacture plastic or metal handles but it permits the manufacture of a metal handle which is competitive in price with plastic handles presently available but made by a more expensive process. Handles of metal are preferred by surgeons because of their weight. This advantage is achieved because the invention uses a simple two-part mold to form the locking member 70.

What is claimed is:

1. The method of making a handle for a surgical blade comprising the steps of
   providing a first lower mold member having a shape to form the lower portion of a handle,
   a vertical split post rising from said first mold member at one portion thereof, said split post including two vertical posts separated by a space and having upper ends in the form of lateral tabs,
   providing a second upper mold member having a shape to form the upper portion of the handle and having a flat wall cooperating with said lateral tabs,
   assembling the first and second mold members to form a mold,
   filling said mold with molten metal,
   said split post forming a blade locking member having a vertical wall formed in said space and two side tabs formed by said lateral tabs.

2. The method of making a metal handle for a surgical blade comprising
   providing a first mold part having a configuration for forming the lower portion of a blade handle and having at one location therein a vertical split pin including two spaced apart vertical posts having flat coplanar top surfaces, forming cutouts in said coplanar top surfaces to form ledges in said vertical posts below said top surfaces, and providing a second mold part having a configuration for forming the upper portion of said handle and including a post having a flat lower surface adapted to cooperate with said flat coplanar surfaces of said vertical posts and said split pin to form a locking member including a vertical wall formed by the space between said two vertical posts and two lateral tabs extending from said vertical wall and formed by the cutouts formed in said two vertical posts.

* * * * *